United States Patent [19]

Kenna

[11] Patent Number: 4,589,883
[45] Date of Patent: May 20, 1986

[54] FEMORAL HIP PROSTHESIS

[75] Inventor: Robert V. Kenna, Hackensack, N.J.

[73] Assignee: Pfizer Hospital Products Group, Inc., New York, N.Y.

[21] Appl. No.: 501,215

[22] Filed: Jun. 6, 1983

[51] Int. Cl.⁴ .............................................. A61F 1/05
[52] U.S. Cl. .................... 623/22; 128/92 C; 128/92 CA
[58] Field of Search .................. 8/1, 1.9, 1.91, 1.912, 8/1.913; 128/92 C, 92 CA

[56] References Cited

U.S. PATENT DOCUMENTS

| | | | |
|---|---|---|---|
| 3,102,536 | 9/1963 | Rose et al. ............................. | 128/92 |
| 3,320,951 | 5/1967 | Wittebol ................................ | 128/92 |
| 3,818,512 | 6/1974 | Shersher ................................ | 3/1 |
| 3,874,003 | 4/1975 | Moser et al. .......................... | 3/1 |
| 3,875,593 | 4/1975 | Shersher ................................ | 3/1 |
| 3,965,490 | 6/1976 | Murray et al. ........................ | 3/1.913 |
| 4,012,796 | 3/1977 | Weisman et al. ..................... | 3/1.91 |
| 4,080,666 | 3/1978 | Fixel ..................................... | 3/1.91 |
| 4,406,023 | 9/1983 | Harris .................................... | 3/1.913 |
| 4,435,854 | 3/1984 | Keller ................................... | 3/1.913 |

*Primary Examiner*—Richard J. Apley
*Assistant Examiner*—David J. Isabella
*Attorney, Agent, or Firm*—Charles J. Knuth; Peter C. Richardson; Harold W. Ordway

[57] ABSTRACT

A femoral hip prosthesis comprises a stem component generally divided into a proximal portion and a substantially longer distal portion. The stem has a slight posterior bow along its length. The proximal portion includes a slight twist of from about 5° to 15°, the twist extending in a direction from the anterior to the posterior face of the stem through the medial face thereof. The characteristics of the stem provide a glove fit when inserted into a prepared intermedullary canal in the femur.

14 Claims, 12 Drawing Figures

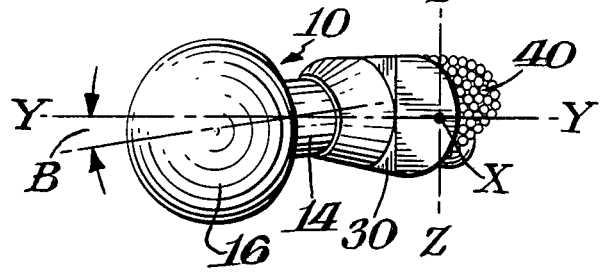
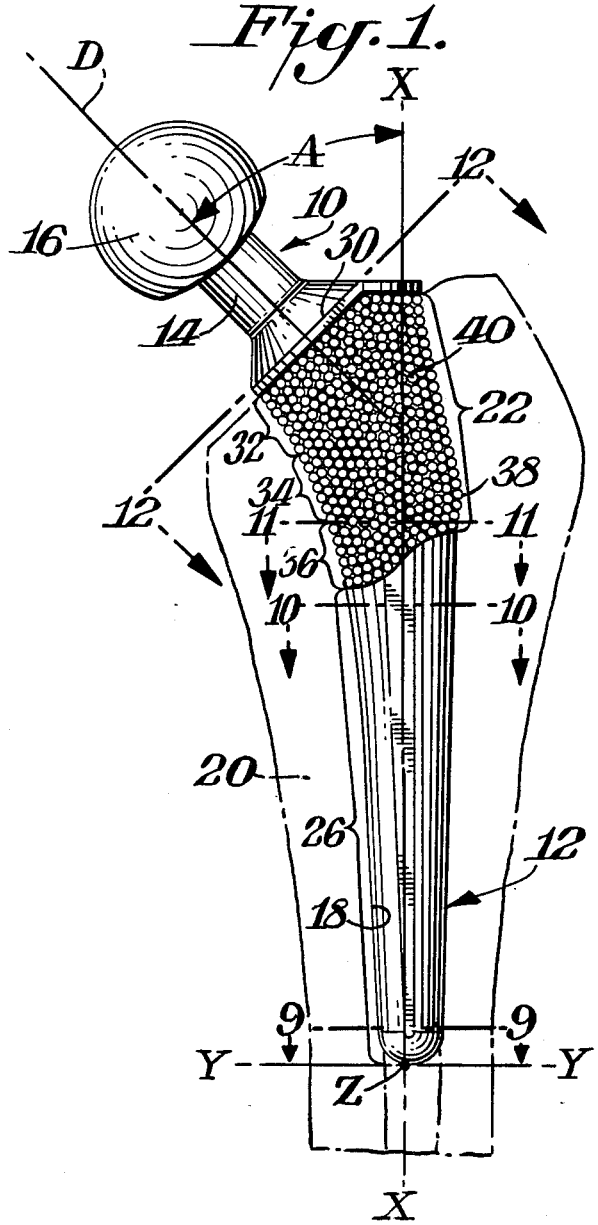
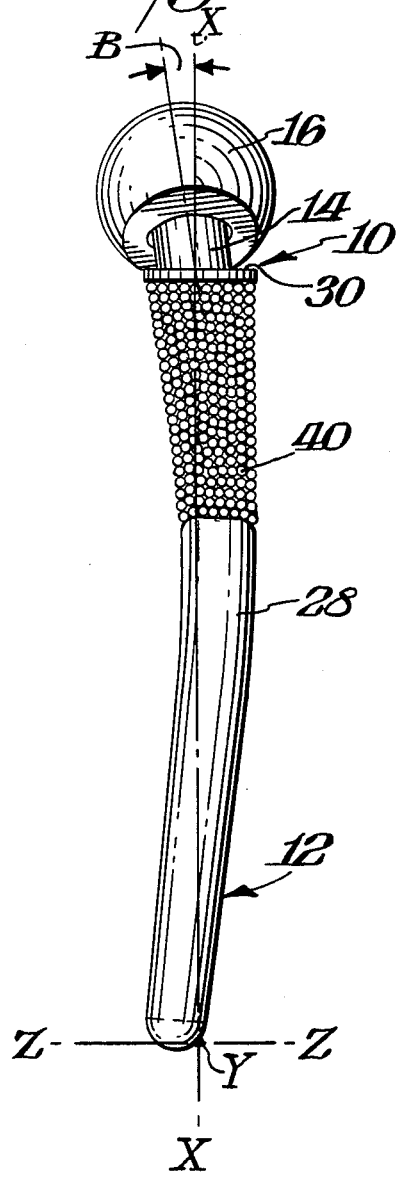

FEMORAL HIP PROSTHESIS

BACKGROUND OF THE INVENTION

The present invention relates to a femoral hip prosthesis, and more particularly to a femoral hip stem component.

Hip arthroplasty procedure includes anesthesia and patient placement on a table in proper orientation. The patient's body is then stabilized, scrubbed, prepared and draped. An incision is made and the subcutaneous tissue is divided. Appropriate soft tissue is excised and/or divided for exposure and dislocation of the hip. After the femoral head is dislocated from its associated acetabulum, the head is rotated for better exposure. A femoral neck osteotomy is then performed wherein the head and neck are cut away from the femur shaft. Next, the intermedullary canal is prepared to accommodate the hip stem component of the prosthesis and, ultimately, the stem is anchored within the intermedullary canal.

Prior to the present invention, numerous femoral inserts have been proposed for use in hip joint prostheses. Generally, each includes a polished spherical head or capitulum mounted upon a stem, which is inserted into the intermedullary canal of the femur. Often, the inserts are cemented within the canal to hold them fast against the applied forces and loads. Such inserts are described, for example, in U.S. Pat. Nos. 3,102,536, 3,320,951, 3,818,512, 3,874,003, 3,875,593, 3,965,490, 4,012,796 and 4,080,666.

The characteristics of the spacing or interface between the exterior surface of the femoral stem and the interior contour of the prepared cavity in the intermedullary canal play an important role in properly anchoring the insert to the femoral bone. A stem of sufficient length has long been recognized as desirable since it provides increased surface area for cementing within the canal and increased resistance to rotation. However, long stems require large intermedullary cavities, particularly at the calcar leading into the canal, since the overall surface thereof makes it impossible for the insert to pass into the canal without a significantly oversized entranceway. Such cavities result in large gaps or voids between the outside surface of the inserted stem and the inside surface of the cavity. Heretofore, a glove fit between a femoral stem and the intermedullary cavity together with superior anchoring of the stem and resistance to rotation have been considered difficult to achieve.

SUMMARY OF THE INVENTION

Accordingly, an object of the present invention is a femoral hip prosthesis having a stem component that forms a glove fit when inserted into the intermedullary canal of a femur, the stem being properly anchored in place and having significant resistance to rotation.

In accordance with the present invention, a femoral hip prosthesis comprises a stem component generally divided into a proximal portion and a substantially longer distal portion. The stem has a slight posterior bow along its length. The proximal portion has a slight twist of from about 5° to 15°, the twist extending in a direction from the anterior to the posterior face of the stem through the medial face thereof.

Preferably, the length of the distal portion is from about 2 to 3 times that of the proximal portion, as measured along the medial face, and the twist generally commences at the boundary of the distal and proximal portions. Moreover, the twist preferably extends throughout the proximal portion and is about 9°. The exterior surface of the proximal portion preferably includes a porous coating to stimulate ingrowth of bone.

The proximal portion of the stem may be generally equally divided into proximal, central and distal segments, with a lateral flare provided on the distal segment for wedge-engaging action with the femoral bone when the stem is inserted therein. A neck extends from the proximal segment of the proximal portion of the stem, the neck having an axis at an angle of about 45° to the general orientation of the stem. Preferably, the neck is anteverted at the angle of from about 5° to 15°, and a capitulum may be secured to the neck by a Morse fit.

BRIEF DESCRIPTION OF THE DRAWING

Novel features and advantages of the present invention in addition to those mentioned above will become apparent to those skilled in the art from a reading of the following detailed description in conjunction with the accompanying drawing wherein:

FIG. 1 is a front elevational or anterior view of a left femoral hip prosthesis, according to the present invention;

FIG. 2 is a top plan view of the prosthesis shown in FIG. 1;

FIG. 3 is a right side elevational or lateral view of the prosthesis shown in FIG. 1;

DETAILED DESCRIPTION OF THE INVENTION

Figure 4:
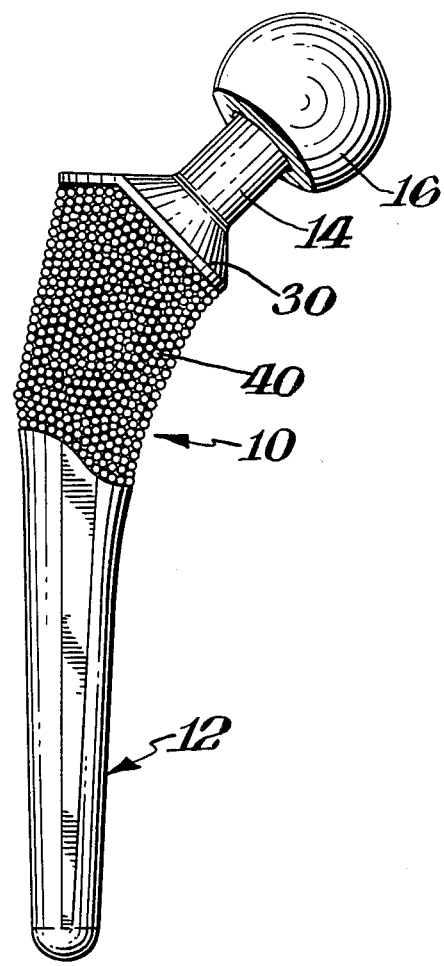
FIG. 4 is a rear elevational or posterior view of the prosthesis shown in FIG. 1.

Referring in more particularity to the drawing, a femoral hip prosthesis 10 includes a stem component 12 having a neck 14 to which a capitulum 16 is secured. FIGS. 1-6 illustrate a left hip prosthesis having an anterior face (FIG. 1), a posterior face (FIG. 4), a lateral face (FIG. 3) and a medial face (FIG. 5). As explained more fully below, the stem 12 tightly fits within a prepared intermedullary cavity 18 in the left femur or femoral bone 20. The fit of stem 12 within cavity 18 is glove-like without any void or gap therebetween.

The stem 12 is generally divided into a proximal portion 22 and a substantially longer distal portion 26. The length of the distal portion 26 is preferably from about 2 to 3 times the length of the proximal portion 22 as measured along the medial face (FIG. 5). As shown best in FIGS. 3 and 5, stem 12 has a slight posterior bow 28 along its length. The posterior bow 28 may be a curve having a radius of about 16 inches, for example, and aids in securing the stem 12 to femur 20 while preventing rotation relative to the femoral bone 20.

The proximal portion 22 includes a slight twist or rotational distortion which generally commences at the boundary between distal portion 26 and proximal portion 22 and continues in an upward direction to the shoulder 30 forming the upper boundary of proximal portion 22. This total twist of generally from about 5° to 15°, preferably from about 7° to 12° and especially about 9°, in proximal portion 22 extends in a clockwise direction when prosthesis 2 is viewed in top plan (FIG. 2). Starting at the boundry between proximal portion 22 and distal portion 26, the twist in proximal portion 22 starts from the anterior face and turns in the direction of the medial face. Hence, the twist is in a direction from the anterior face to the posterior face of stem 12 through the medial face thereof.

Figure 12:
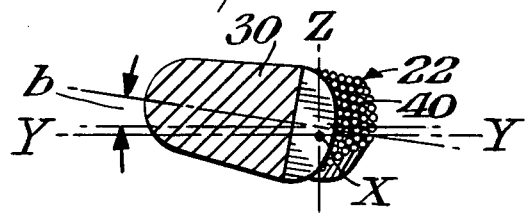
FIG. 12 is a sectional view taken along line 12—12 of FIG. 1.
Figure 11:
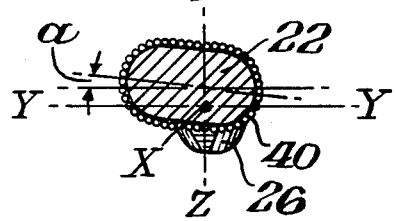
FIG. 11 is a sectional view taken along line 11—11 of FIG. 1.
Figure 10:
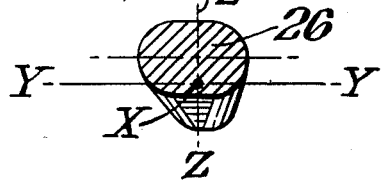
FIG. 10 is a sectional view taken along line 10—10 of FIG. 1.
Figure 9:
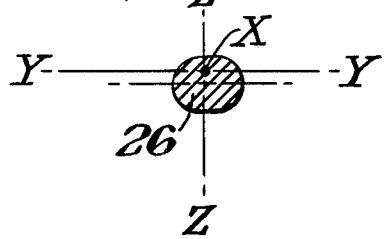
FIG. 9 is a sectional view taken along line 9—9 of FIG. 1.

This is best shown in the sectional views of FIGS. 9–12 wherein it can be seen that distal portion 26 has no twist. FIG. 1 together with the sectional views of FIGS. 9–12 show that the horizontal Y and Z axes cross each other at 90°, and that the point of intersection forms the vertical axis X. Utilizing these coordinates, it is readily apparent from FIGS. 9 and 10 that distal portion 26 of stem 12 is without twist. However, FIG. 11 clearly shows that the twist has commenced in the proximal portion 22 amounting to angle a of about 4° at that elevation. Continuing, the upper extreme of proximal portion 22 exhibits the especially preferred total twist angle b of about 9°, and such is shown in FIG. 12.

The proximal portion 22 of stem 12 may be generally equally divided into a proximal segment 32, a central segment 34 and a distal segment 36. For reasons explained more fully below, distal segment 36 includes a flare or enlargement 38 on the lateral side thereof. When stem 12 is inserted into femur 20, flare 38 wedgingly engages the adjacent bone to thereby load and stress the bone, which promotes bone growth into and around prosthesis 10. In this regard, the entire outside surface of proximal portion 22 includes a porous coating 40 for the ingrowth of bone and tissue.

Figure 5:
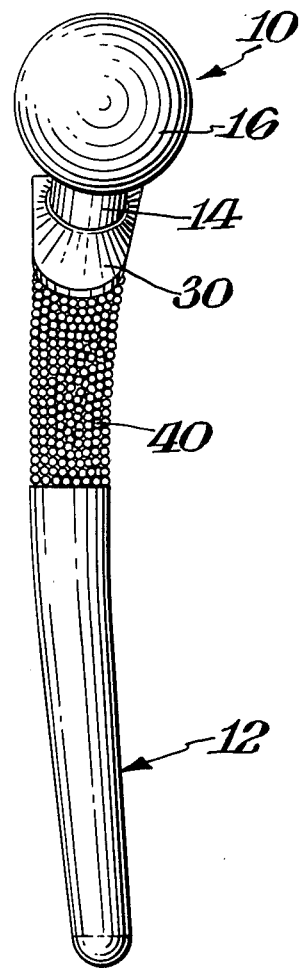
FIG. 5 is a left side elevational or medial view of the prosthesis shown in FIG. 1.
Figure 6:
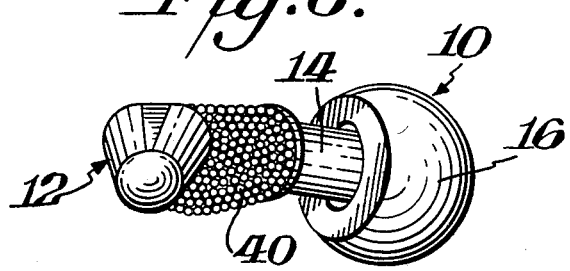
FIG. 6 is a bottom plan view of the prosthesis shown in FIG. 1.
Figure 7:
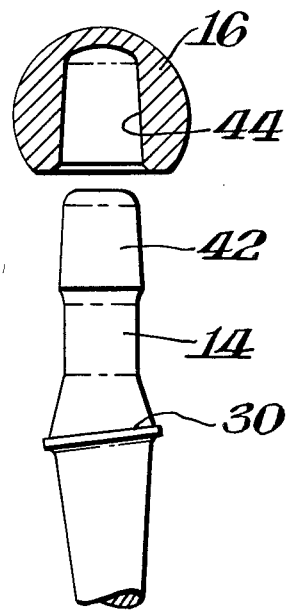
FIG. 7 is an exploded view of the prosthesis shown in FIG. 1 with the capitulum shown in section.
Figure 8:
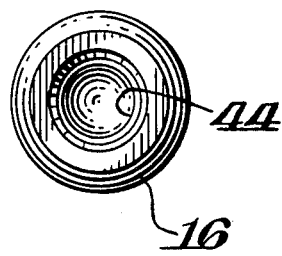
FIG. 8 is a bottom plan view of the capitulum.

As shown best in FIGS. 1 and 4, neck 14 of prosthesis 10 is at an angle A of about 45° to the general orientation of stem 12. The neck 14 has a tapered free end portion 42 which cooperates with a tapered internal socket 44 in the capitulum 16. The tapering characteristics of end portion 42 and socket 44 are such that a Morse fit results when the capitulum 16 is secured onto the neck 14. As is well known, the capitulum 16 is in the form of a polished spherical element which articulates with the natural acetabulum, or an acetabular prosthesis if the natural acetabulum has been replaced.

Neck 14 and its associated capitulum 16 are anteverted at an angle B, generally of from about 5° to 15° and preferably from about 9° to 15°. As shown in FIGS. 2 and 3, this anteversion is about 9°; as such, capitulum 16 is angled slightly toward the anterior by about 9°. Such anteversion places capitulum 16 in the best possible position for articulation with the natural acetabulum or acetabular prosthesis.

Femoral hip prosthesis 10 is implanted within the femur 20 following femoral neck osteotomy and proper formation of the intermedullary cavity 18 into which stem 12 of the prosthesis 10 is to be inserted. In forming the intermedullary cavity 18, a portion of the cancellous tissue near the end of the femur 20 initially is cut away with an appropriate cutting tool (not shown). Following such removal, a rasp (not shown) having the same general shape as stem 12 is driven into the intermedullary canal of femur 20. The rasp is then withdrawn from the femur 20 and the stem 12 introduced into the thus formed intermedullary cavity 18. Stem 12 passes into intermedullary cavity 18 without violating or interrupting the newly formed contour shaped by the rasp. The posterior bow 28 together with the twist in the proximal portion 22 enables such insertion of the stem into intermedullary cavity 18 and results in a glove fit substantially free of gaps or voids between the exterior surface of the stem 12 and the interior contour of the prepared cavity 18.

Porous coating 40 on proximal portion 22 stimulates ingrowth of bone, and the lateral flare 38 accelerates this anchoring process. Since tensile loading is greatest at the lateral surface of proximal portion 22, lateral flare 38 increases the surface area at that location to load and stress the adjacent bone and thereby promote ingrowth. Additionally, the wedge engaging action of the lateral flare 38 against the femoral bone 20 significantly contributes to the anchoring of the stem 12 within the intermedullary cavity 18, and bone cement is not needed.

With prosthesis 10 in two pieces comprising stem 12 and capitulum 16, multiple neck lengths can be obtained with each stem 12 by using capitulums 16 with different internal sockets 44. For example, when a long neck length is desired, the internal socket 44 in the capitulum 16 may be short, and with a long internal socket 44 a shorter neck length is achieved with the same stem 12. Both stem 12 and capitulum 16 may be fabricated of, for example, cobalt/chromium/molybdenum or titanium by techniques known in the art.

I claim:

1. A femoral hip prosthesis comprising a stem component with an anterior face, a posterior face, a lateral face and a medial face and having a proximal portion and a substantially longer distal portion, the stem being noncircular in cross section and exhibiting a slight posterior bow along its length, the stem further including a twist of from about 5° to 15° in the proximal portion, the twist extending in a direction from the anterior to the posterior face about the longitudinal axis of the stem, thereby providing a more accurate fit between the stem and an intramedullary cavity and positive resistance to rotation of the stem within the cavity.

2. A femoral hip prosthesis as in claim 1 wherein the length of the distal portion is from about 2 to 3 times the length of the proximal portion as measured along the medial face.

3. A femoral hip prosthesis as in claim 1 wherein the twist generally commences at the boundary of the distal and proximal portions.

4. A femoral hip prosthesis as in claim 3 wherein the twist extends throughout the proximal portion.

5. A femoral hip prosthesis as in claim 4 wherein the twist is about 9°.

6. A femoral hip prosthesis as in claim 1 wherein the exterior surface of the proximal portion includes a porous coating.

7. A femoral hip prosthesis as in claim 6 wherein the proximal portion is generally equally divided into a proximal segment, a central segment and a distal segment with a flare on the lateral face of the distal segment.

8. A femoral hip prosthesis as in claim 1 wherein the proximal portion is generally equally divided into a proximal segment, a central segment and a distal segment with a lateral flare on the distal segment.

9. A femoral hip prosthesis as in claim 8 including a neck extending from the proximal segment, the neck having an axis at an angle of about 45° to the general orientation of the stem.

10. A femoral hip prosthesis as in claim 9 wherein the neck is anteverted at an angle of from about 5° to 15°.

11. A femoral hip prosthesis as in claim 10 including a capitulum secured to the neck.

12. A femoral hip prosthesis as in claim 11 wherein the capitulum and the neck are secured together by a Morse fit.

13. A femoral hip prosthesis as in claim 1 wherein the stem is generally oblong in cross section.

14. A femoral hip prosthesis as in claim 1 wherein the twist extends in a direction from the anterior through the medial to the posterior face about the longitudinal axis of the stem.

* * * * *